United States Patent
Hendrickson et al.

(10) Patent No.: US 6,571,792 B1
(45) Date of Patent: Jun. 3, 2003

(54) SMART MODULAR ANESTHESIA RESPIRATORY SYSTEM

(75) Inventors: Carl H. Hendrickson, Madison; Denise L. Pernetti, Cottage Grove; James N. Mashak, Sun Prairie; Brian C. Michell, Madison; Terrance P. Sullivan, Madison; Ross G. Garland, Madison, all of WI (US)

(73) Assignee: Datex-Ohmeda, Inc., Madison, WI (US)

(*) Notice: Subject to any disclaimer, the term of this patent is extended or adjusted under 35 U.S.C. 154(b) by 340 days.

(21) Appl. No.: 09/042,241

(22) Filed: Mar. 13, 1998

Related U.S. Application Data
(60) Provisional application No. 60/062,055, filed on Oct. 15, 1997.

(51) Int. Cl.[7] .............................................. A61M 15/00
(52) U.S. Cl. ........................... 128/203.12; 128/202.22; 128/202.27; 128/205.23
(58) Field of Search ..................... 128/202.27, 202.22, 128/203.12, 909, 911, 205.23

(56) References Cited

U.S. PATENT DOCUMENTS

| | | | | |
|---|---|---|---|---|
| 2,586,677 A | * | 2/1952 | Marrett | 128/203.12 |
| 2,872,167 A | * | 2/1959 | Pratt | 128/203.12 |
| 3,815,596 A | * | 6/1974 | Keener et al. | 128/909 |
| 4,825,860 A | * | 5/1989 | Falb et al. | 128/203.12 |
| 4,991,576 A | * | 2/1991 | Henkin et al. | 128/202.27 |
| 5,121,746 A | * | 6/1992 | Sikora | 128/911 |
| 5,293,865 A | * | 3/1994 | Altner et al. | 128/203.12 |
| 5,413,097 A | * | 5/1995 | Birenheide et al. | 128/202.22 |
| 5,626,129 A | * | 5/1997 | Klimm et al. | 128/202.27 |
| 5,651,357 A | * | 7/1997 | Braatz et al. | 128/202.27 |
| 5,682,876 A | * | 11/1997 | Pernetti et al. | 128/202.27 |
| 5,692,494 A | * | 12/1997 | Pernetti et al. | 128/202.27 |
| 5,810,001 A | * | 9/1998 | Genga et al. | 128/202.27 |
| 5,983,896 A | * | 11/1999 | Fukunaga et al. | 128/202.27 |

\* cited by examiner

*Primary Examiner*—Aaron J. Lewis
(74) *Attorney, Agent, or Firm*—Andrus, Sceales, Starke & Sawall, LLP

(57) ABSTRACT

An anesthesia system wherein the respiratory system is fitted with interchangeable patient circuit modules that allows a generic fitting in the machine to have affixed, hereto, a module that has ports suitable for connection to various patient breathing circuits. As such, the anesthesia machine can have the patient circuit modules easily changed and thus be adaptable for use with patient breathing circuits such as the circle system, the open/nonrebreathing circuit and the Bain or Mapleson D circuits. A detector system is provided that identifies that particular patient module installed in the anesthesia machine to alert the main CPU and to thus provide the correct flow sensing schemes and flows to the patient breathing circuit then being used.

10 Claims, 7 Drawing Sheets

SMART MODULAR ANESTHESIA RESPIRATORY SYSTEM

RELATED APPLICATIONS

This application is based upon U.S. Provisional Patent Application No. 60/062,055 filed Oct. 15, 1997.

BACKGROUND

The present invention relates to anesthesia machines, and more particularly, to an anesthesia respiratory system that provides a modular form of connector to the patient breathing circuit used to administer an anesthetic to a patient undergoing surgery.

In general, anesthesia systems are utilized in operating rooms and comprise various equipment necessary to anesthetize the patient, support or control respiration, and maintain the patient in that state until the operation is completed and it is possible to terminate the introduction of the anesthetic agent.

Such systems comprise various pressure regulators, flow control devices, gas mixing devices and vaporizers to vaporize a volatile liquid anesthetic into life support gases and to introduce these anesthetic laden gases (fresh gas) to the patient via the respiratory system. The respiratory system provides manual and automatic means to control or support the patients breathing of the fresh gas mixture. The patient is connected to the system by means of a face mask or other device and which interfaces with the respiratory system via a patient breathing circuit that may typically have an inspiratory limb tube through which the gases are introduced into the patient and an expiratory limb tube that conveys the exhaled gases from the patient.

In such systems, the patient breathing circuit conveys the fresh gas from the respiratory system to the patient where the face mask or endotracheal tube connects that patient breathing circuit to the patient. One difficulty, however, with anesthesia machines is the concern that various different types of patient breathing circuits are used for differing reasons by clinicians and therefore the anesthesia machine must be able to operate easily and be adaptable to the various patient breathing circuits. Examples of commonly used patient breathing circuits include the circle type, the open/non-rebreathing circuit and the Bain or Mapleson D circuits. Each are well known circuits commercially available and are used for particular circumstances. Changing from one breathing circuit to another is cumbersome involving a number of different attachments for mounting, fresh gas, sensors, ventilator, etc. depending on the particular anesthesia machine.

Accordingly, the anesthesia machine also handles the various monitoring functions, supplies of gas and the like differently depending on the patient breathing circuit being used. One means of dealing with the differing patient breathing circuits is to utilize a modular form of connector to the anesthesia machine where the respiratory system is standard but has a plurality of interchangeable breathing circuit modules that can be easily inserted for the particular patient breathing circuit being used.

Therefore, if the clinician is utilizing the standard circle patient breathing circuit, that particular breathing circuit module is inserted into the anesthesia machine and provides all the necessary connections to the respiratory system and to the circle patient breathing circuit. Similarly, a separate breathing circuit module is insertable into the machine for other patient breathing circuits, as previously indicated.

As noted, each patient breathing circuit poses differing conditions to the anesthesia machine, that is, a differing fresh gas flow, differing positions and functions of flow sensors and the like and therefore, if the modular approach is used with the anesthesia machine, it is important for the basic central processor unit (CPU) in the anesthesia machine to be able to know which module or patient breathing circuit is being employed so that the processor can determine the correct flow sensor algorithm to activate for volume monitoring or what flows of fresh gas are appropriate for the patient breathing circuit in use and also alert the user as to the module in use

SUMMARY OF THE INVENTION

The anesthesia system of the present invention therefore corrects the aforementioned difficulties by providing an easily changeable modular respiratory system that identifies the particular breathing circuit module that is installed in the machine and therefore alerts the central processing unit of the anesthesia machine, and hence the user, as to the identity of the patient breathing circuit so that the correct flows are sensed and the correct flow of fresh gas and the like are provided to the patient.

DETAILED DESCRIPTION OF THE INVENTION

Figure 1:
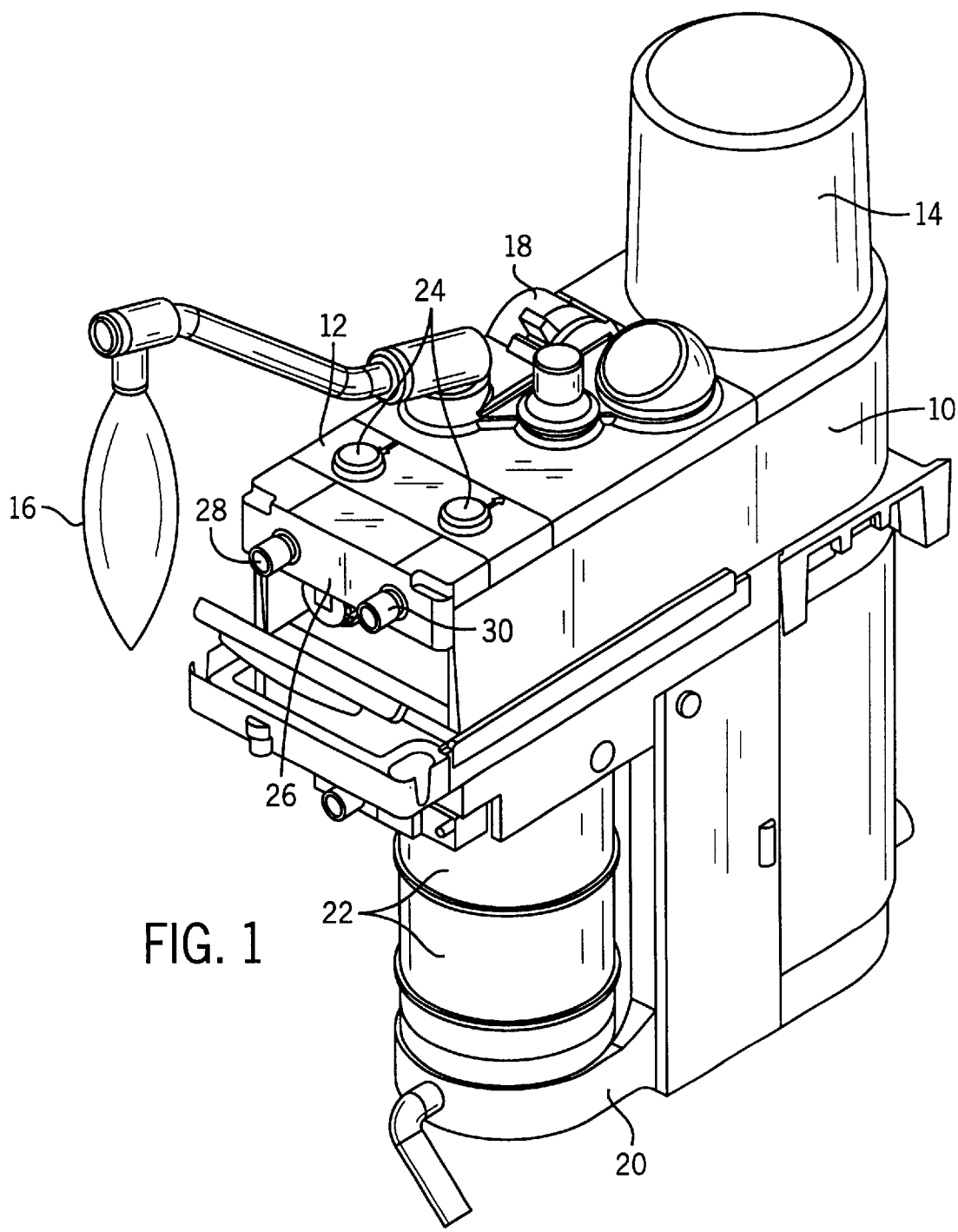
FIG. 1 is an isometric view of the respiratory system portion of an anesthesia machine having breathing circuit modules that can be identified in accordance with the present invention.

Referring now to FIG. 1, there is shown an isometric view of the respiratory system 10 that is part of an anesthesia machine and having a breathing circuit module 12 installed for use with a particular patient breathing circuit. The overall anesthesia machine showing the location of the particular portion is shown and described in copending U.S. Pat. No. 5,692,494 of Pernetti et al and the disclosure of which is incorporated herein.

Shown connected to the respiratory system 10 is a bellows container 14 that contains a bellows that cooperates with a mechanical ventilator to provide powered breaths to the patient. Alternatively a flexible breathing bag 16 is included and which can be manually squeezed or contracted by the clinician to provide that breath to the patient. A switch 18 is provided on the respiratory system 10 and is conveniently located so that the clinician can select between using a mechanical ventilator to breathe the patient or manually manipulate the flexible breathing bag 16.

As shown, there is a carbon dioxide absorber assembly 20 which includes carbon dioxide absorbent canisters 22 to rid the recirculating gases from the patient of carbon dioxide so that some of the same expired gases can be reintroduced to the patient when the circle breathing circuit module is in use. The respiratory system 10 contains various other components of the overall system including check valves 24 that allow flow in the proper direction to and from the patient. A flow sensor module 26 interfits to the breathing circuit module 12 and includes ports 28, 30 for providing a breathing gas to and from, respectively, the particular patient breathing circuit that is being used at the time.

Figure 2:
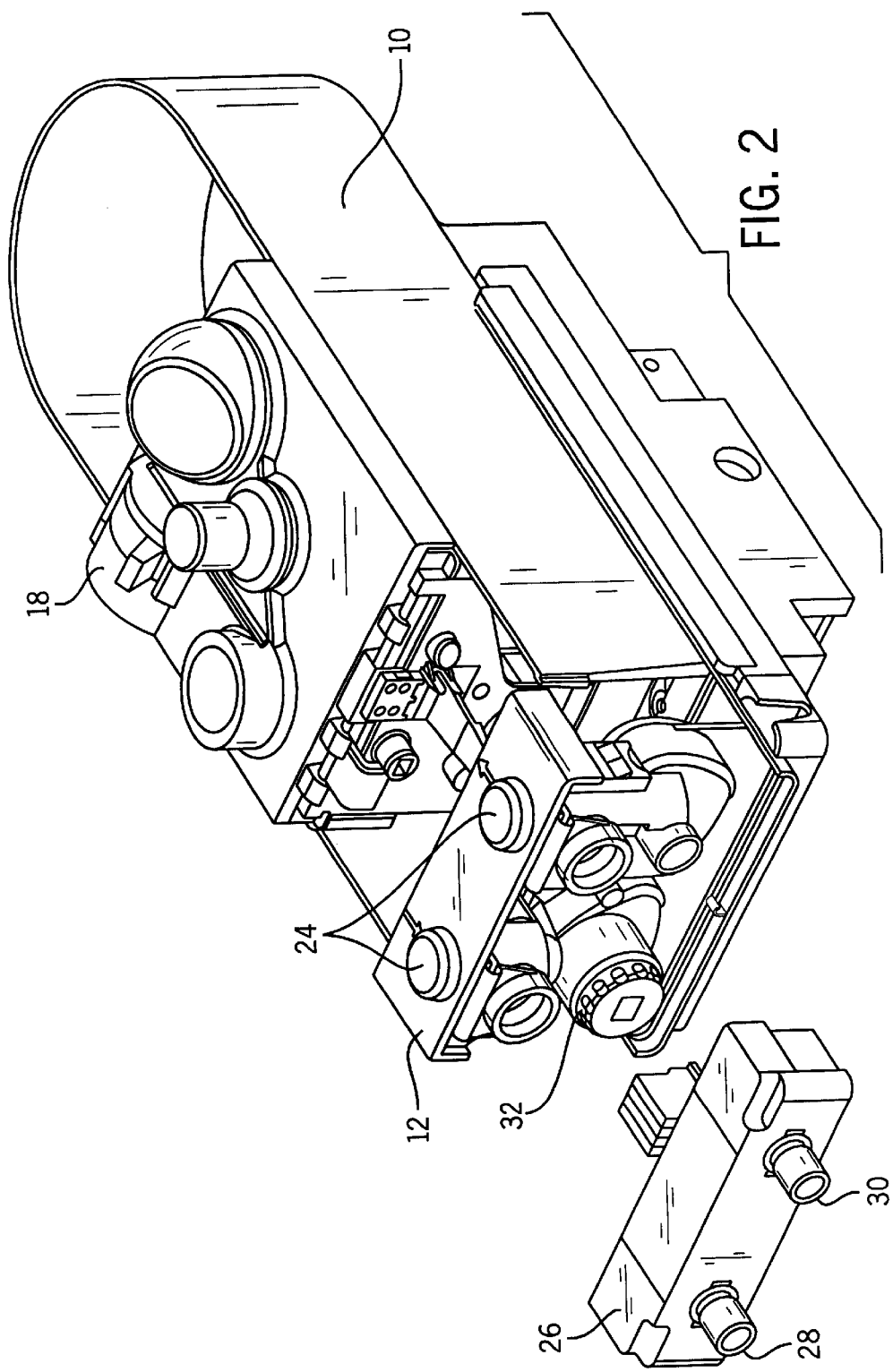
FIG. 2 is an isometric, exploded view of a typical breathing circuit module and showing its installation on the respiratory system.
Figure 3A:
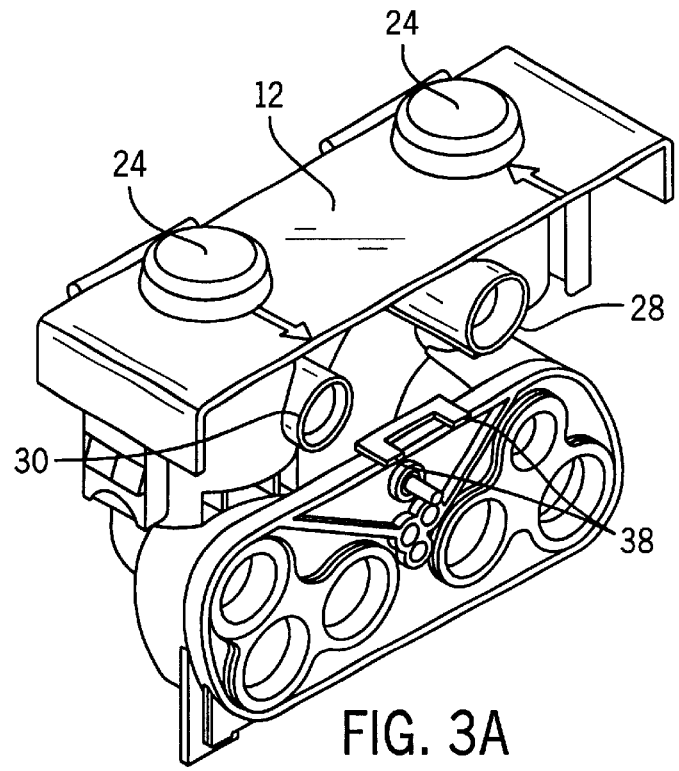
FIGS. 3A–B, 4A–B and 5A–B are isometric views of breathing circuit modules usable with the present invention.
Figure 3B:
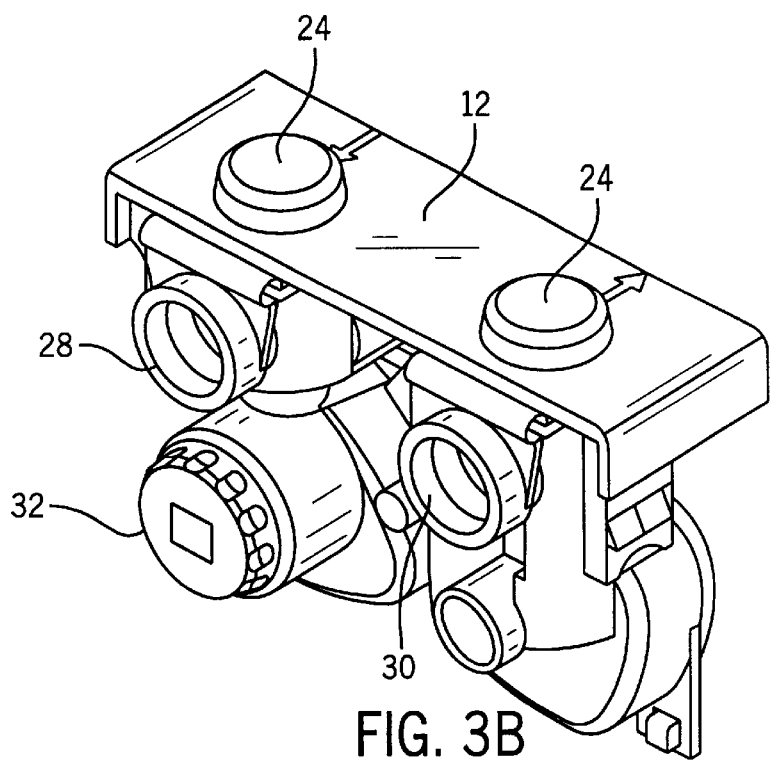
Figure 4A:
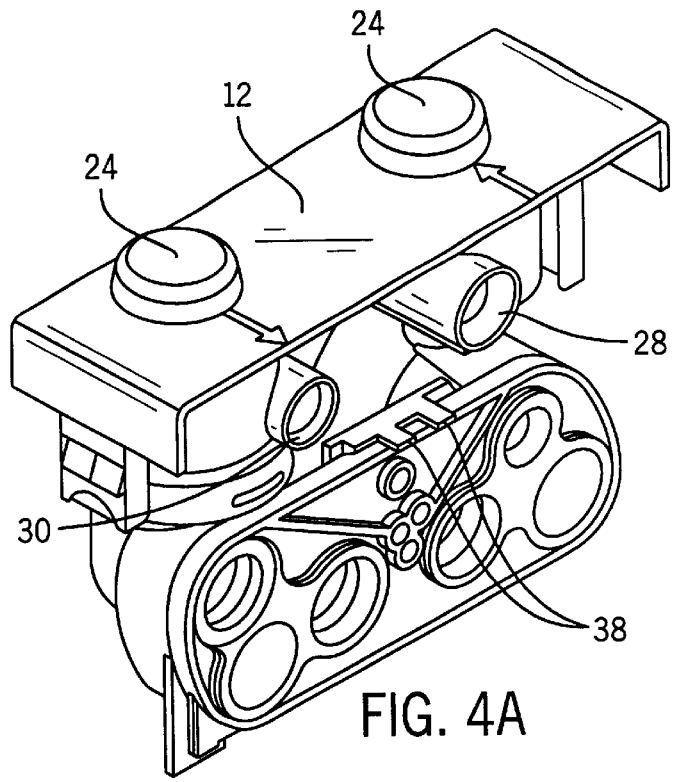
Figure 4B:
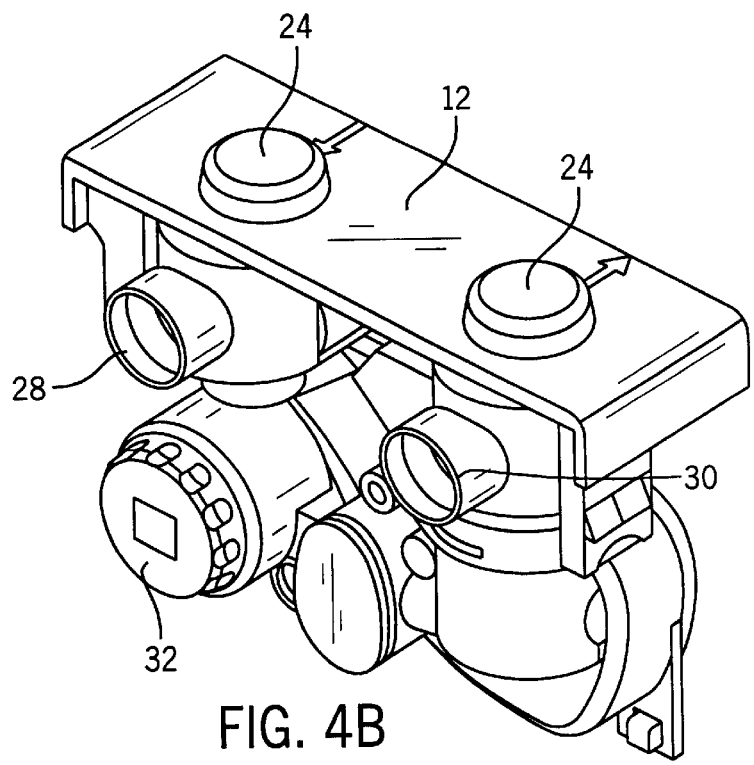
Figure 5A:
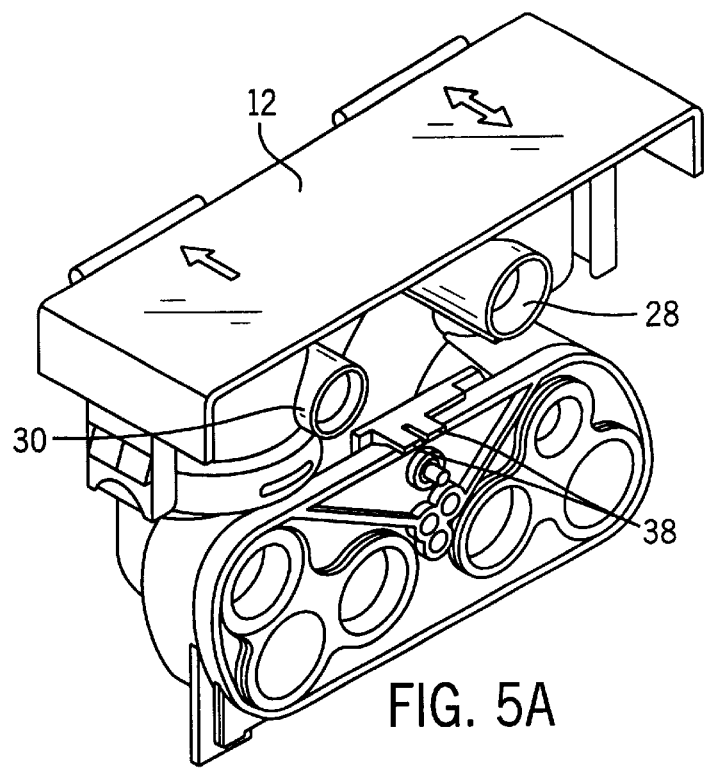
Figure 5B:
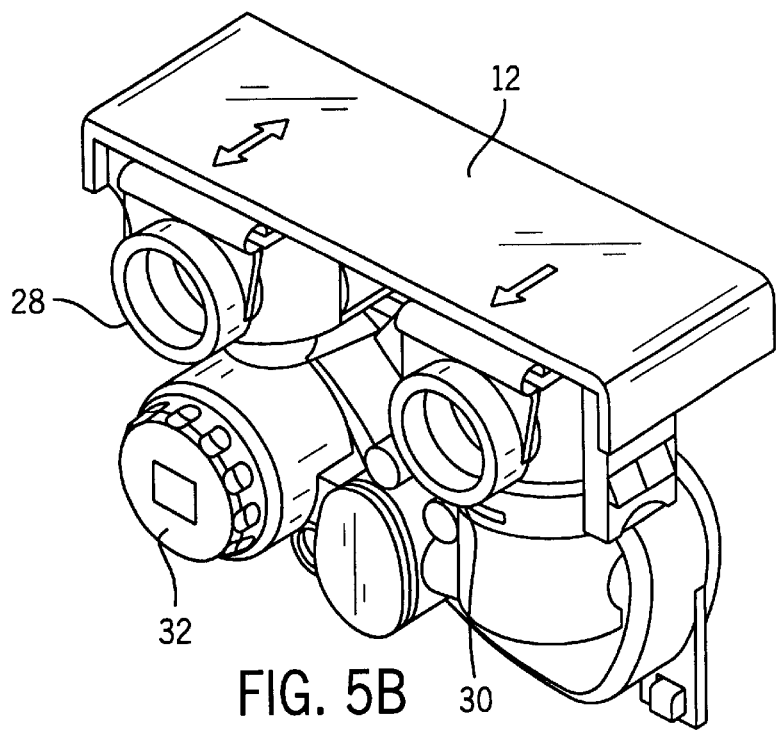

Turning now to FIG. 2, there is shown an isometric view of a breathing circuit module 12 in an exploded view showing how it is affixed to the respiratory system 10 and, in the preferred embodiment, the breathing circuit module 12 is affixed by means such as a thumb screw 32 that interfits with internal threads, (not shown) in the respiratory system 10 so that the appropriate pneumatic connection can be made between the breathing circuit module 12 and the respective manifold passages 36 (FIG. 6) of the respiratory system 10. Accordingly, another pneumatic connection is made between the breathing circuit module 12 and the fresh gas connection 34 from the anesthesia machine. (See FIG. 6)

In FIGS. 3A–B, 4A–B and 5A–B, there are isometric views of the various breathing circuit modules 12 for the user that are a circle breathing circuit, an open or non/rebreathing patient circuit and a Bain or Mapleson D breathing circuit, respectively. The ports 28 and 30 are internally connected to provide the flows and receive the flows from each of those circuits. For example, if a circle patient breathing circuit is being used (FIGS. 3A–B) with the respiratory system 10, the breathing circuit module 12 is connected to the respiratory system 10 such that the ports 28 and 30 are connected so as to supply the gas and receive the exhaled gas that is typical of a circle patient breathing circuit.

Since it is important for the anesthesia machine to know which particular patient breathing circuit is attached to the anesthesia machine, i.e. to match the appropriate flows to the patient breathing circuit and to provide the proper monitoring of the flows, it is necessary for the anesthesia machine to ascertain which breathing circuit module 12 is in position and affixed to the respiratory system 10.

As a part of ascertaining the identity of the particular breathing circuit module 12, a plurality of tabs 38 extend outwardly from each of the breathing circuit modules shown in FIGS. 3–6, each of which is in a unique configuration so as to allow the identification of that particular breathing circuit module 12. As shown in the preferred embodiment, two tabs 38 extend from each of the breathing circuit modules 12 and their specific use will be later explained.

Figure 6:
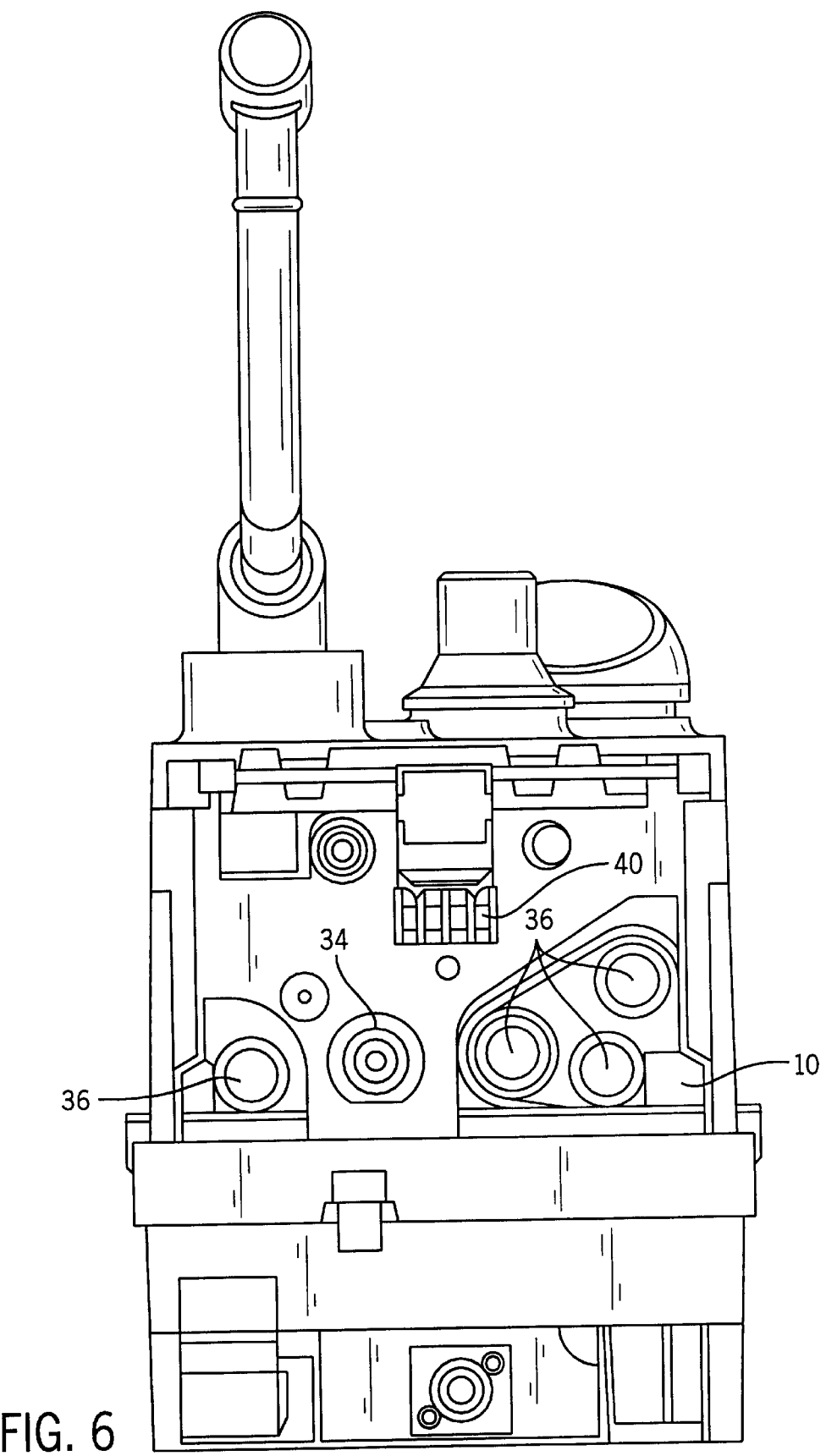
FIG. 6 is a frontal view of a respiratory system with the breathing circuit modules removed.
Figure 7:
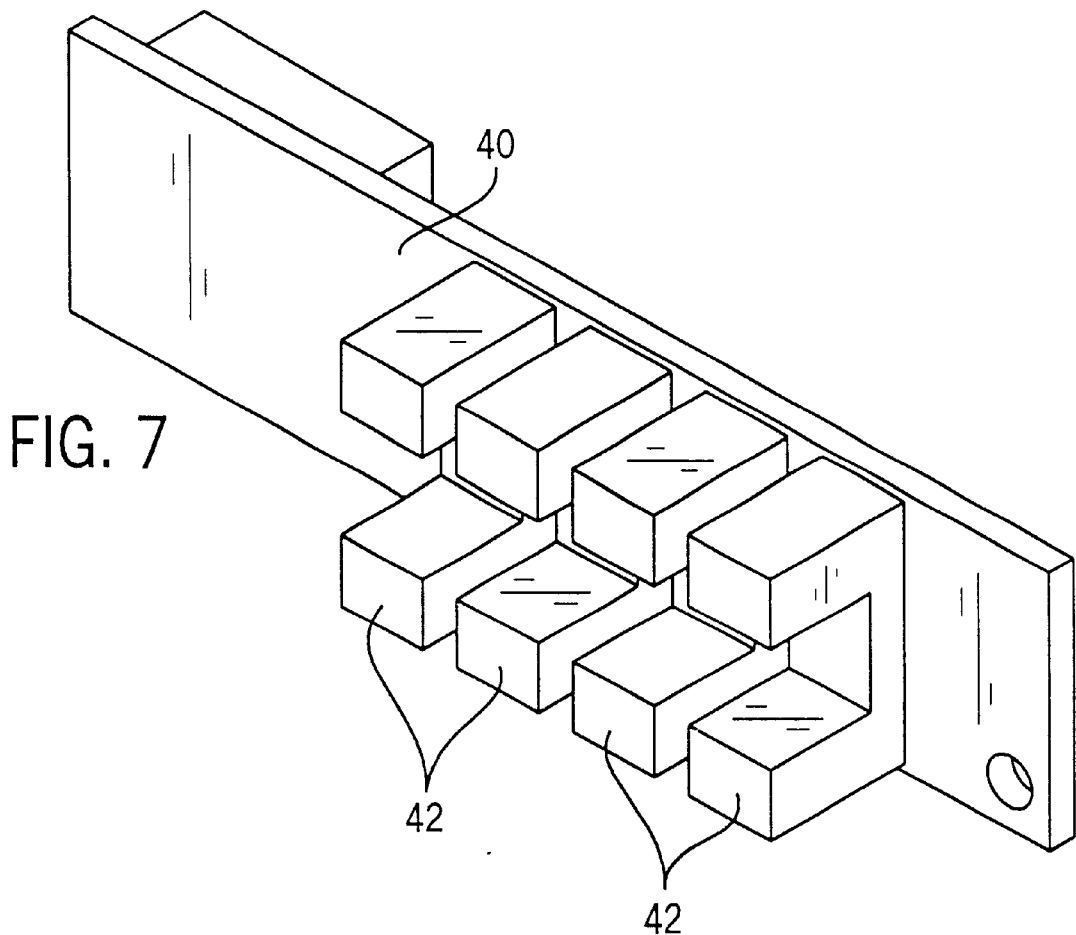
FIG. 7 is an enlarged isometric view of a sensor array that is constructed to be used with the present invention.

Taking now, FIG. 6, in conjunction with FIGS. 3–5, there is shown a frontal view showing the respiratory system 10 open to receive a breathing circuit module. As can be seen, there are manifold passages 36 that provide the pneumatic breathing connections between the breathing circuit modules 12 and the respiratory system 10. Also shown is the fresh gas connection 34 from the anesthesia machine. As can also be seen a sensor array 40 is located on the respiratory system and which receives the tabs 38 of the particular breathing circuit module and can identify that patient circuit module depending upon the position of those tabs 38. Referring also to FIG. 7, there is shown an enlarged isometric view of a typical sensor array 40 that is used with the preferred embodiment and which has a plurality of sensors 42. Each of the sensors 42 may comprise a light source and a light detector such that the light emanating from the light source will normally fall upon the light detector, however, when one of the tabs 38 is inserted between the light source and the light detector, that light is interrupted and an identification of the particular breathing circuit module can be made.

That information is supplied to a central processing unit (CPU) in the anesthesia machine so that the CPU can take the appropriate action, such as adapt the anesthesia machine flows and flow sensor algorithms to be appropriate for the particular patient breathing circuit being used at the time.

While the present invention has been set forth in terms of a specific embodiment, it will be understood that the present patient circuit module identification system herein disclosed may be modified or altered by those skilled in the art to other configurations and that information used for other purposes. Accordingly, the invention is to be broadly construed and limited only by the scope and spirit of the claims appended hereto.

We claim:

1. An anesthesia machine connectable to a selected one of a plurality of patient breathing circuits, the patient breathing circuits having one or more conduits providing differing characteristic gas flow paths for supplying fresh gas containing an anesthetic agent and for supplying and receiving breathing gas to and from a patient, said anesthesia machine comprising:

an anesthesia delivery unit (10) having ports (34, 36) providing and receiving breathing gases for the patient and providing the fresh gas containing an anesthetic agent;

a flow sensor module (26), said flow sensor module having ports (28, 30) suitable for connection to the conduit or conduits of a selected one of the plurality of patient breathing circuits;

a selected one of a plurality of interchangeable patient circuit modules (12) provided in accordance with the selected one of the plurality of patient breathing circuits, said selected patient circuit module being interposed intermediate said anesthesia delivery unit and said flow sensor module, said selected patient circuit module containing flow paths extending between said anesthesia delivery unit and said flow sensor module for establishing the characteristic breathing gas and fresh gas flow paths for the selected one of the plurality of patient breathing circuits; and a detector for providing an indication of which one of the plurality of patient circuit modules is interposed intermediate said anesthesia delivery unit and said flow sensor module, said detector comprising first means (38) mounted on said patient circuit module and second means (40) mounted on said anesthesia delivery unit, said first and second means being so mounted on said patient circuit module and said anesthesia delivery unit, respectively, as to be brought into proximity with each other when said patient circuit module is interposed intermediate said anesthesia delivery unit and said flow sensor module, said first and second means coacting when in proximity with each other for providing said indication.

2. An anesthesia machine as defined in claim 1 wherein said detector comprises an optical detection means.

3. An anesthesia machine as defined in claim 2 wherein said optical detection means comprises an array of individual optical detectors (42), the means (38) on said patient circuit module operating certain ones of the optical detectors of said array to provide said indication of which one of the plurality of patient circuit modules is interposed intermediate said anesthesia delivery unit and said flow sensor module.

4. An anesthesia machine as defined in claim 3 wherein said individual optical detectors comprise a light source and a light detector forming a light path between said source and detector, said patient circuit module having means interrupting the light path between certain ones of said individual optical detectors when said patient circuit module is interposed intermediate said anesthesia delivery unit and said flow sensor module.

5. An anesthesia machine as defined in claim 4 wherein each of said patient circuit modules includes a unique configuration of one or more tabs extending outwardly therefrom for interrupting the light paths of said optical detectors when said selected patient circuit module is interposed intermediate said anesthesia delivery unit and said flow sensor module.

6. An anesthesia machine as defined in claim 1 wherein said anesthesia delivery unit includes a central processing unit, said detector being coupled to said central processing unit to provide the indication of which one of the plurality of patient circuit modules is interposed intermediate said anesthesia delivery unit and said flow sensor module.

7. An anesthesia machine as defined in claim 6 wherein said central processing unit contains anesthesia delivery unit operating algorithms for the plurality of patient breathing circuits and means for selecting an operating algorithm in accordance with the indication provided by said detector.

8. An anesthesia machine as defined in claim 1 wherein said patient circuit module is further defined as containing flow paths suitable for establishing the characteristic gas flow paths for a non-rebreathing or open patient breathing circuit in which the gas flow paths of the patient breathing circuit are formed such that the breathing gas and fresh gas are discharged from the patient breathing circuit.

9. An anesthesia machine as defined in claim 1 wherein said patient circuit module is further defined as containing flow paths suitable for establishing the characteristic gas flow paths for a re-circulating patient breathing circuit in which the gas flow paths of the patient breathing circuit are formed such the that breathing gas and fresh gas can be re-circulated in the patient breathing circuit.

10. An anesthesia machine as defined in claim 1 wherein said patient circuit module is further defined as containing flow paths suitable for establishing the characteristic gas flow paths for a Bain or Mapleson D patient breathing circuit.

* * * * *

UNITED STATES PATENT AND TRADEMARK OFFICE
CERTIFICATE OF CORRECTION

PATENT NO. : 6,571,792 B1  Page 1 of 1
DATED : June 3, 2003
INVENTOR(S) : Carl H. Hendrickson et al.

It is certified that error appears in the above-identified patent and that said Letters Patent is hereby corrected as shown below:

<u>Title page,</u>
Item [56], insert:

-- [56]  References Cited
  U.S. PATENT DOCUMENTS
  3,687,137   8/1972   Johnson
  FOREIGN PATENT DOCUMENTS
  643,978   3/1995   EPO
  742,027   11/1996   EPO
  338,518   10/1989   EPO --

Signed and Sealed this

Thirtieth Day of December, 2003

JAMES E. ROGAN
*Director of the United States Patent and Trademark Office*